United States Patent [19]

Nonnenmann

[11] 4,149,314
[45] Apr. 17, 1979

[54] ORTHODONTIC BRACKETS WITH PIVOTAL FASTENINGS

[76] Inventor: Michael J. Nonnenmann, 3228-91st Ave. W., Rock Island, Ill. 61201

[21] Appl. No.: 769,931

[22] Filed: Feb. 18, 1977

[51] Int. Cl.² ............................................. A61C 7/00
[52] U.S. Cl. ................................................... 32/14 A
[58] Field of Search ...................... 32/14 A; 24/249 R

[56] References Cited

U.S. PATENT DOCUMENTS

| 2,548,864 | 4/1951 | Brusse | 32/14 A |
|---|---|---|---|
| 2,665,480 | 1/1954 | Johnson | 32/14 A |
| 2,767,469 | 10/1956 | Gladstone | 32/14 A |
| 3,044,217 | 7/1962 | Berry | 24/249 R |
| 3,084,437 | 4/1963 | Neger | 32/14 A |
| 3,543,404 | 12/1970 | Rubin | 32/14 A |
| 3,686,758 | 8/1972 | Kesling | 32/14 A |
| 3,748,740 | 7/1973 | Wildman | 32/14 A |
| 3,871,096 | 3/1975 | Wallshein | 32/14 A |
| 3,959,880 | 6/1976 | Andrews | 32/14 A |

Primary Examiner—Russell R. Kinsey
Assistant Examiner—John J. Wilson
Attorney, Agent, or Firm—Glenn H. Antrim

[57] ABSTRACT

The wings on one side of a slot for an arch wire have slanting, oblong openings to receive a pivotal side of a generally rectangular fastening. The fastening is pivotally mounted in the openings; the pivotal side slides inwardly within the openings to allow the opposite latching side of the fastening to be passed over opposite latching wings; and then the pivotal side slides outwardly to retain the latching side within hook-shaped inner surfaces of the latching wings. The ends of the fastening cross over and retain an arch wire in a slot intermediate the wings. Auxiliary springs to provide rotational force on torque may be integral parts of the fastening.

4 Claims, 10 Drawing Figures

U.S. Patent  Apr. 17, 1979  4,149,314
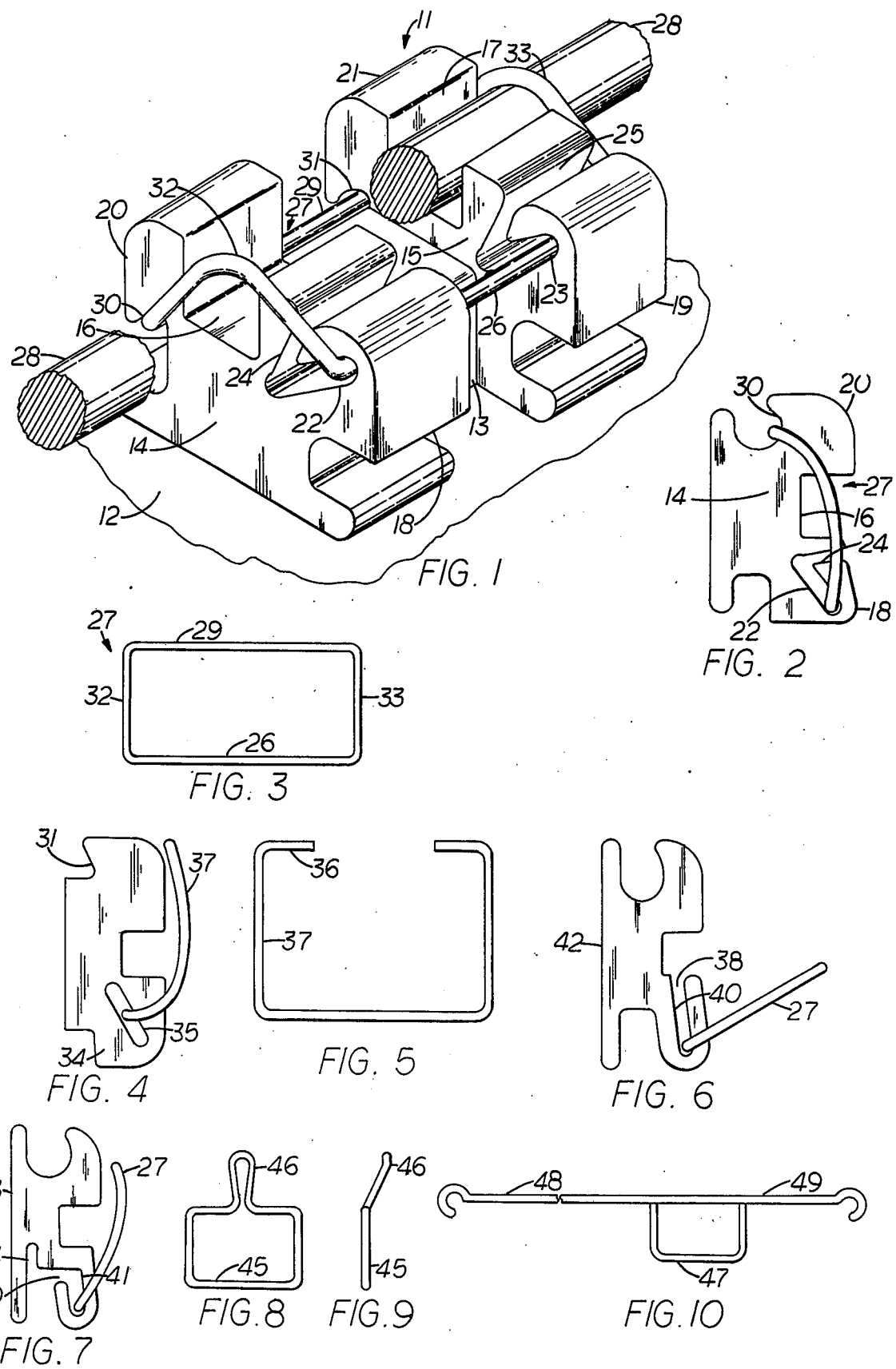

ORTHODONTIC BRACKETS WITH PIVOTAL FASTENINGS

BACKGROUND OF THE INVENTION

This invention relates to orthodontic brackets and particularly to brackets having pivotal fastenings for retaining arch wires.

A common type of orthodontic bracket has a central slot for receiving an arch wire. The arch wire is contained within the slot by a small ligating wire of soft metal that is wound over the arch wire and underneath a pair of wings on each side of the slot and is secured by twisting its ends tightly together. The brackets that use ligating wires are generally the edgewise type in which the central slot accommodating the arch wire is rectangular.

As teeth gradually move toward a desired position during treatment, the relative positions or the sizes of brackets, arch wires, and auxiliaries such as elastics and springs are changed to aid in continued desired direction of movement of the teeth in their arch. Therefore, in addition to the time and skill required for the original installation of the ligating wires with their twisted ends, additional time is required to tie the ligating wires whenever orthodontic devices require adjustment or replacement.

Various brackets having latching members to replace the ligating wires have been proposed. A successful bracket of the latching type must not only be latched quickly but must be smooth enough to prevent irritation to buccal tissue, must be versatile, and must be readily cleaned. The brackets proposed previously have not been commonly accepted.

SUMMARY OF THE INVENTION

The bracket according to the present invention has a pivotal, generally rectangular fastening. One side of the fastening is pivoted on a spaced pair of pivotal wings on one side of a slot for an arch wire, and when the fastening is rotated over an arch wire, the other side is latched beneath latching wings on the opposite side of the slot. The pivotal side of the fastening passes through oblong slanted openings of the pivotal wings and slides along the openings as the latching side is moved outwardly over the latching wings and inwardly to a latched position. After the fastening is latched, the outward force of the arch wire on the overlying portions of the fastening presses the side functioning as a hinge outwardly in the slanting slots, and the outward movement of the hinge causes the latching portion of the fastening to move inwardly against hook-shape portions of the latching wings. The fastening can be unlatched by pressing toward the center of the base on its pivotal side and pressing away from the base on its latching side so that the latching side can be moved outwardly over the adjacent wings.

When the present bracket is applied to a tooth that is so far out of alignment that the latching of the pivotal fastening is difficult or impossible, ligating wires can be applied over the arch wire and under the wings in a usual manner. Subsequently, when the tooth has become more nearly aligned with the arch wire, the ligating wire can be replaced with a pivotal fastening. Preferably, a channel through the surface of the pivotal wings to the slanted opening for the hinge is provided near the inner end of the oblong opening so that the hinge of the fastening can be readily inserted or removed by passing it through the channel.

Special springs for applying either rotational force or torque to a tooth can be readily integrated with the fastening. For example, for applying torque, a short spring member may extend from the center of the latching side toward the gingiva to bear against the tooth for causing the arch wire to move the occlusive portion of the tooth outwardly. Either the pivotal side or the latching side of the fastening may have a spring member extending outwardly to be hooked beneath or over the arch wire to cause rotation of a tooth.

BRIEF DESCRIPTION OF THE DRAWING

FIG. 1 is a perspective view of a preferred orthodontic bracket of this invention;

FIG. 2 is an end view of the bracket of FIG. 1;

FIG. 3 is a plan view of the fastening of the bracket of FIG. 1 to show its continuous rectangular shape;

FIG. 4 is an end view of another embodiment of the orthodontic bracket;

FIG. 5 is a plan view of the fastening of FIG. 4 to show its discontinuous pivotal side;

FIGS. 6 and 7 are end views of different embodiments of the orthodontic bracket to show different passages to oblong openings for the pivotal portions of the fastenings;

FIG. 8 is a plan view of a fastening with a spring auxiliary extending therefrom;

FIG. 9 is a side view of the fastening of FIG. 8; and

FIG. 10 is a fastening having extending auxiliaries for applying a couple to a tooth that is to be rotated.

DESCRIPTION OF THE PREFERRED EMBODIMENTS

In FIG. 1, an orthodontic bracket 11 is secured to a tooth 12 in a usual manner by being attached to a band about the tooth or, as shown, by being attached directly to the tooth by adhesive. At each end of a rectangular base 13, a perpendicularly projecting portion 14 or 15 has a slot 16 or 17 respectively with an outwardly facing opening for receiving an arch wire 28. Wings 18 and 19 project laterally outwardly in one direction from the respective slots 16 and 17, and on the other side of the bracket wings 20 and 21 project outwardly opposite wings 18 and 19, respectively. The wings 18 and 19 have respective oblong openings 22 (FIG. 2) and 23 for pivotally receiving a pivotal side 26 of a rectangular wire fastening 27 (FIG. 3). Each of the oblong openings 22 and 23 extends slantingly inwardly at a small angle with respect to the base 13 for retaining the fastening 27 latched as described below. Each of the wings 18 and 19 has a passageway 24 and 25 respectively through its outer surface inwardly to connect to the inward end of the respective opening 22 and 23. The lower face of each of the wings 18–21 has a groove or indentation facing the surface on which the bracket 11 is secured such that the inward surface of the wing functions as a hook. For a tooth that is far out of alignment, ligating wires can be wound in a usual manner beneath the outer portions of the wings 18–21, but usually a fastening 27 is used, and its latching side 29 is held by the hook-shaped portions 30 and 31 formed by the indentations in the inward surfaces of the wings 20 and 21, respectively. Preferably as shown in FIG. 1, the ends 32 and 33 of the fastening 27 is bowed upwardly in its latched position from the openings 22 and 23 and from the hook-shaped portions 30 and 31 to position an outer curved portion over the arch wire.

The orthodontic bracket 11 is cast or machined from stainless steel and different brackets have different dimension to accommodate different sizes of teeth and provide for different types of correction. The bases 13 of different brackets have different thicknesses to accommodate teeth of different thickness such that the lingual arch of the teeth is smooth. A selection of different lengths is required for teeth of different widths. To provide for desired forces of rotation or torque on a tooth, the slots 16 and 17 may be different depths, and both slots 16 and 17 may be slanted somewhat from the perpendicular direction with respect to the base.

After the brackets 11 have been aligned as desired on an arch of teeth and an arch wire 28 has been installed in a usual manner, the hinge side 26 of the fastening 27 for each of the brackets 11 is moved through the passageways 24 and 25 to the oblong openings 22 and 23. The fastening 27 is then rotated inwardly such that its ends 32 and 33 cross over the arch wire 28, and the latching side 29 is pressed over the wings 20 and 21 until it is located within the hook-shaped portions 30 and 31 of the wings 20 and 21 respectively. During final positioning of the latching side 29, the pivotal side 26 of the fastening 27 is moved outwardly within the oblong openings 22 and 23. When a new arch wire is to be installed, the fastening 27 for each of the brackets associated with the arch wire may be unlatched by moving its pivotal side 26 inwardly within the slots 22 and 23 and pressing outwardly on the latching side 29 to release the latching side from the wings 20 and 21. If a fastening 27 needs to be replaced, its pivotal side 26 can be readily removed from the bracket through the passageways 24 and 25.

Another embodiment of an orthodontic bracket is shown in FIGS. 4 and 5. The bracket 34 has a straight, rectangular base and the pivotal opening 35 has a closed edge. The center of the pivotal side 36 of the fastening 37 is cut away to provide pivotal portions that are to be spread apart while the free ends of the pivotal side 36 are inserted in the openings 35. Either this type of fastening or the continuous type of FIG. 3 can be cast or formed from wire of stainless metal.

In FIGS. 6 and 7, respectively, different locations of passageways 38 and 39 to the pivotal openings 40 and 41 of the brackets 42 and 43 are shown. In FIG. 6, the passageway 38 to the opening 40 is between the inner end of the opening and the slot into which an arch wire is to be placed; and in FIG. 7, the passageway 39 for the opening 41 is directed toward the base of the bracket 43. A slot 44 adjacent the passageway 39 in the base of the bracket is used when a ligating wire is desirable.

Springs for applying a torque or a rotating force to teeth can be integrated with the rectangular fastenings for the present brackets as shown in FIGS. 8-10. In FIGS. 8 and 9, an auxiliary spring 46 extends from the latching side of a rectangular fastening 45 for applying torque to a tooth. When the rectangular fastening 45 is latched as described above, the extension 46 bears inwardly against the tooth. Usually the pivotal side of the bracket is toward the gingiva, but it can be placed oppositely as shown in FIG. 1 such that the spring 46 can bear on the tooth adjacent the gingiva. According to FIG. 10, an auxiliary spring, or a pair of auxiliary springs, can be an extension of either the pivotal side or the latching side of a fastening 47. When a pair of springs 48 and 49 extend in opposite directions as shown in FIG. 10, the outer end of one spring can be fastened under the arch wire, and the end of the other spring can be fastened over the arch wire in a usual manner to form a couple for rotating a tooth to which is attached a bracket having the fastening 47.

Although the orthodontic bracket shown in the accompanying drawing and described above relates to the edgewise type in which two separated points are tied to an arch wire, the length may be decreased and only one pair of wings on opposite sides of a slot be used to obtain a single-point or Begg-type bracket. The pivotal wing need not have the hook-shaped portion for use of ligating wire, and therefore the portion for the pivotal opening may be a rectangular or other conveniently shaped side extension.

I claim:

1. An orthodontic bracket comprising:

a base, a projecting portion extending outwardly from each end of said base, each of said projecting portions having a pivotal mounting portion and a latching wing extending laterally as wings in respective opposite directions from a respective one of said projecting portions, said pivotal mounting portions extending in the same direction and being spaced apart and said latching wings extending in the same direction and being spaced apart, each of said projection portions having a slot facing outwardly with respect to said base, said slots being in line for receiving an arch wire intermediate said respective pivotal mounting portions and said latching wings, said wings having smooth rounded outer edges, a fastening removably fastened between said pivotal mounting portions and said latching wings to extend over and retain an arch wire within said slot, said fastening having rod-like sides arranged rectangularly, one of said sides of said fastening being a hinge portion and the opposite side being a latching portion, each of said pivotal mounting portions having an opening, said openings of said pivotal mounting portions being aligned to receive said hinge portion of said fastening, said openings in a lateral cross section of said hinge portions being oblong with their longer dimension extending from near the outer edges of said pivotal mounting portions slantingly inwardly at a small angle with respect to said base and toward said base, whereby said hinge portion can be moved inwardly and outwardly along said oblong openings to facilitate latching and unlatching said fastening, each of said latching wings having a surface facing said base and curving toward said base in an outwardly extending direction to form a hook, said hinge portion being insertable in said openings of said pivotal mounting portions, the ones of said sides adjacent to and connecting said latching portions and said hinge portion being a required length to permit said latching portion to be pressed tightly over said latching wings while said hinge portion is positioned in said openings toward respective ones of said latching wings, said sides adjacent said hinge and said latching portions being bowed outwardly over an arch wire and bearing against said arch wire to retain said fastening in a latched position in which said hinge portion is positioned outwardly within said openings and said latching portion is positioned inwardly beneath said hooks.

2. An orthodontic bracket as claimed in claim 1 in which said pivotal mounting portions have respective grooves facing said base to provide in conjunction with said hooks of said latching wings anchorage for ligating wire to be substituted for said fastening.

3. An orthodontic bracket as claimed in claim 1 having respective passageways through the surfaces of said pivotal mounting portions to said openings thereof to permit insertion of said hinge portion into said openings.

4. An orthodontic bracket as claimed in claim 3 wherein said passageways through said surfaces of said pivotal mounting portions passes through respective portions of the surfaces thereof opposite said base to connect to those ends of said openings adjacent respective ones of said slots.

* * * * *